(12) United States Patent
First et al.

(10) Patent No.: US 7,887,832 B2
(45) Date of Patent: Feb. 15, 2011

(54) POPPING ORAL PHARMACEUTICAL COMPOSITIONS

(75) Inventors: Sigal First, Petach Tivka (IL); Rina Yamin, Rehovot (IL)

(73) Assignee: CTS Chemical Industries, Ltd., Kiryat Malachi (IL)

( * ) Notice: Subject to any disclaimer, the term of this patent is extended or adjusted under 35 U.S.C. 154(b) by 1254 days.

(21) Appl. No.: 10/994,376

(22) Filed: Nov. 23, 2004

(65) Prior Publication Data

US 2005/0089567 A1    Apr. 28, 2005

Related U.S. Application Data

(63) Continuation-in-part of application No. 10/173,814, filed on Jun. 19, 2002, now abandoned, and a continuation-in-part of application No. PCT/IL03/00519, filed on Jun. 18, 2003, and a continuation-in-part of application No. PCT/IL03/00518, filed on Jun. 18, 2003.

(51) Int. Cl.
  *A61K 9/68* (2006.01)
  *A61K 1/17* (2006.01)

(52) U.S. Cl. .................. 424/440; 424/441; 424/442

(58) Field of Classification Search .......... None
  See application file for complete search history.

(56) References Cited

U.S. PATENT DOCUMENTS

| | | | |
|---|---|---|---|
| 3,947,566 A * | 3/1976 | Sarna et al. | ............ 424/45 |
| 3,947,567 A | 3/1976 | Berg, Jr. et al. | |
| 3,947,568 A | 3/1976 | Bates et al. | |
| 3,985,909 A | 10/1976 | Kirkpatrick | |
| 3,985,910 A | 10/1976 | Kirkpatrick | |
| 4,001,457 A | 1/1977 | Hegadorn | |
| 4,241,092 A * | 12/1980 | Halik et al. | ............ 426/96 |
| 4,263,328 A | 4/1981 | Parada et al. | |
| 4,271,206 A | 6/1981 | Fariel et al. | |
| 4,275,083 A * | 6/1981 | Colten et al. | ............ 426/96 |
| 4,289,794 A | 9/1981 | Kleiner et al. | |
| 5,178,878 A | 1/1993 | Wehling et al. | |
| 6,071,539 A * | 6/2000 | Robinson et al. | ............ 424/466 |
| 6,150,424 A | 11/2000 | Breitenbach et al. | |
| 6,310,014 B1 | 10/2001 | Rau | |
| 6,350,470 B1 | 2/2002 | Pather et al. | |
| 6,358,493 B1 | 3/2002 | Birkel et al. | |
| 2001/0022964 A1* | 9/2001 | Leung et al. | ............ 424/49 |

FOREIGN PATENT DOCUMENTS

| | | |
|---|---|---|
| EP | A2 371 228 | 6/1990 |
| WO | WO 99/64555 | 12/1999 |
| WO | WO 00/57858 A1 | 10/2000 |
| WO | WO 02/062152 A1 | 8/2002 |

* cited by examiner

*Primary Examiner*—S. Tran
(74) *Attorney, Agent, or Firm*—Edwards Angell Palmer & Dodge LLP; Peter F. Corless; Nicholas J. DiCeglie, Jr.

(57) ABSTRACT

Disclosed are popping pharmaceutical compositions, which comprise OTC or prescription drug, and popping material. The popping material includes pressurized gas trapped within cavities of a pharmaceutically acceptable material in a manner that allows the gas to escape from the pharmaceutical composition upon dissolution, contact with saliva or shattering of the popping material.

Such an oral pharmaceutical composition may be popular with children that will prefer it on other ones, which do not pop. Methods for preparation of such oral pharmaceutical compositions are also disclosed.

11 Claims, No Drawings

POPPING ORAL PHARMACEUTICAL COMPOSITIONS

The present application is a continuation-in-part (CIP) application of U.S. patent application Ser. No. 10/173,814, PCT/IL2003/000518 and PCT/IL2003/000519, all incorporated herein by reference.

FIELD OF THE INVENTION

This invention relates to oral pharmaceutical compositions and to processes for their preparation.

BACKGROUND OF THE INVENTION

Gasified particles are known in the art as particles that comprise a core material, which encapsulates a pressurized gas that escapes as the core material dissolves or shatters.

Popping candies and confections, namely, candies and confections that include gasified particles are known in the food industry, but not in the pharmaceutical art. The gas release of these products is based on exposure of entrapped gas inside the formulation with water or saliva. This mechanism results in gas eruption that is very quick and strong and gives tingling sensation and popping noise.

Effervescent pharmaceutical compositions for oral administration, such as tablets, capsules, and lozenges are well known in the pharmaceutical art. An effervescent pharmaceutical composition includes compounds which evolve gas by means of a chemical reaction between an acid and a base which takes place upon exposure of the effervescent pharmaceutical composition to water or other fluids. Effervescence is usually used to enhance drug dissolution and for taste improvement. Gas eruption is very slow and gentle.

The present invention provides popping pharmaceutical compositions, which are known neither in the pharmaceutical art, nor in the food industry.

RELATED ART

The following description relates to references that are considered to be relevant as background to the invention. Appearance of a document in this description should not be construed as implying that the document is relevant to the patentability of the invention.

Processes for making gasified particles are known in the art of candy making. For example, processes for making gasified confections are described in the following publications: U.S. Pat. Nos. 3,985,909, 3,985,910 and 4,001,457.

U.S. Pat. No. 4,289,794 describes a method for preparing gasified candy whereby a sugar melt is gasified at superatmospheric pressure and then is cooled below its fusion temperature under superatmospheric pressure to form a gasified candy. As the gasified candy is wetted in the mouth the candy melts and the gas escapes producing an entertaining popping sensation.

U.S. Pat. No. 4,263,328 describes a method of preparation of a tableted confection of gasified candy and mention that such candies may include a breath freshener.

U.S. Pat. No. 4,271,206 describes gasified confection prepared by molding to a predetermined shape.

Pharmaceutical compositions comprising an effervescent agent are described for example, in U.S. Pat. Nos. 6,350,470 and 5,178,878 and in EP 1082106.

WO 00/57858 describes a solid pharmaceutical administration form containing a saliva activated effervescent agents like sodium bicarbonte.

U.S. Pat. No. 3,947,566 describes medicament compositions comprising a medicament and a liquefied gas distributed therethrough in an aerosol dispensing container which may escape from the composition by boiling to produce auditory effects. The exemplified liquefied gas having boiling point of from −50 to 80° F. (−45-27° C.), such as Freon.

U.S. Pat. No. 4,275,083 describes confectionary that includes popping material rubbed in oleaginous substance, such as peanut butter.

U.S. Pat. No. 4,786,502 describes lipid-containing, molded pharmaceutical compositions, comprising: (a) from about 10% to about 50% of a lipid material having a melting point of from about 26° C. to about 37° C.; (b) from about 10% to about 50% of a particulate dispersant material; (c) from about 0.1% to about 3% of an emulsifier; and (d) a safe and effective amount of a pharmaceutical active material; wherein the particulate materials in said composition have a mean particle size of from about 4 microns to about 10 microns, with less than about 10% of the particulates greater than about 30 microns in size.

U.S. Pat. No. 5,573,255 describes a chewable medicinal tableting composition comprising as proportions of the total composition: capric triglyceride: about 30 to about 95% by weight, and a medicinally active ingredient: up to 60% by weight.

SUMMARY OF THE INVENTION

The present invention provides, according to the first aspect thereof, an oral pharmaceutical composition comprising an active ingredient and a thermodynamically stable pressurized gas, the pressurized gas being trapped in cavities within a pharmaceutically acceptable material, in a manner that allows its escape upon dissolution, contact with saliva or shattering of the pharmaceutically acceptable material, wherein the active ingredient is a prescription drug or a drug sold over the counter.

The active ingredient may be included in the material trapping the pressurized gas in the cavities thereof.

A pharmaceutical composition according to the invention may comprise more than one active ingredient.

Preferable oral pharmaceutical compositions according to the invention include a fatty matrix, that may be melt and molded with the pharmaceutically acceptable material that includes the pressurized gas (hereinafter the popping material) and the active ingredient. Such pharmaceutical compositions may be prepared without the need to compress the popping material and therefore, without risking losing the popping effect of the popping material. Such oral pharmaceutical compositions may be, for instance, in the form of lozenges or chewable administrations forms.

The term "pressurized gas" refers to a gas at a pressure more than 1 atmosphere.

The gas trapped in the cavities may be any pharmaceutically acceptable inert gas. The term "inert" indicates that the gas does not react with the pharmaceutically acceptable material, in the cavities of which the pressurized gas is trapped and the other ingredients included in the pharmaceutical composition during preparation, storage or use.

Non limiting examples of gases suitable for the preparation of the oral pharmaceutical composition are carbon dioxide, nitrogen, air, helium, argon, and neon.

Non limiting examples of suitable materials for trapping therein the gas are sugars such as glucose, fructose, sucrose, lactose, maltose, corn syrup and mixtures thereof.

The oral pharmaceutical composition of the present invention may further comprise coloring, flavoring and other excipients.

It should be noted that the term "pharmaceutical composition" should be construed in a broad sense and includes any composition administered for the purpose of achieving a therapeutic effect in humans or animals, and sold carrying a label as to the intended indication, whether as a prescription drug or over the counter (OTC).

"An oral pharmaceutical composition" is a composition, the swallowing of which is permissible. Such a pharmaceutical composition is usually intended to be given through the mouth, for swallowing, for treating the mouth cavity, etc.

The term "active ingredient" should be construed in a broad sense as including any ingredient considered to have a therapeutic effect when delivered to a subject in need thereof and further being regulated by drug authorities like: CDER, EMEA, TAG etc. Pharmaceutical active ingredients may act systemically upon swallowing, locally when present in the buccal cavity, etc.

The active ingredient may be an analgesic, an antipyretic, an anti-inflammatory, an expectorant, an antibiotic, an antihypertensive, an anti-histamine, an anti-anginal, an antiepileptic, an anxiolytic, an antipsychotic, anti-allergic, an antidepressant, a hormone, a steroid, an hypolipidaemic, a diuretic, etc. Thus, it may be a drug such as paracetamol, diphenhydramine, dextromethorphan, lidocaine, loratadine, ibuprofen, pseudoephedrine, enalapril, calcium carbonate, isosorbide-mononitrate, enalapril maleate, sodium valporate, aspirin, alprazolam, amitriptyline, amoxicillin, benzocaine, celecoxib, dexamethazone, famotidine, lansoprazole, simvastatin, lorazepam, testosterone, verapamil, etc., or a veterinary active ingredient such as nitroscanate, abamectin, ivermectin, etc. The active ingredient may be taste masked, for instance by coating or microencapsulation.

A fatty matrix, is a matrix made substantially of fatty acids, fatty acid alcohols, hydrogenated vegetable oils, glyceric esters of fatty acids, cocoa butter, and the like. Preferably, the melting point of the fatty matrix is between 30 to 40° C., such that it melts in the mouth.

According to one embodiment, the fatty matrix coats particles of the popping material.

According to another embodiment, the gasified particles and the active ingredient are mixed with the fatty matrix.

The oral pharmaceutical composition according to the present invention may have different administration forms, such as a tablet, powder, pellets, capsule, syrup, oil, suspension, gel, drops and various candy-like forms.

In one non-limiting example, candy-like administration form may be a chocolate bar including gasified particles and an active ingredient.

Preferably, an oral pharmaceutical composition according the present invention, which includes a fatty matrix, is in the form of a tablet, capsule, or a bar, when tablet is most preferable.

An oral pharmaceutical composition according to the present invention may have benefits in many circumstances, for instance, it may be popular with children that will like the popping sensation and will be more willing to take a popping pharmaceutical composition than one that does not create a popping sensation. The escape of the gas does not only produce a pleasant sensation but may also stimulate saliva production, thereby providing additional saliva to aid dissolution in the mouth. Similarly, it may be used to enhance dissolution of tablets or powders in a drinking liquid. Such tablets may be useful for the elderly or swallow-problem population. It may be used in semi-solids, oils, suspensions or solid preparations to enhance disintegration or dissolution of the active ingredients either in the mouth or in the stomach or intestine.

Particles which contain trapped pressurized gas may be coated by any suitable material that would protect them from direct contact with water or moisture during storage. Preferably, such a coating material dissolves when the escape of the gas is required. Suitable coating materials may be for instance, cocoa butter that melts in the mouth, biodegradable polymers typically used for gastrointestinal delivery of drugs (such as enteric polymer that dissolves in the intestine), etc.

An oral pharmaceutical composition according to the present invention which includes a fatty matrix has the double benefit of having long shelf-life (despite of the water-sensitivity of the popping material and possibly also of an active ingredient) and being easy to swallow. Thus, it may be used for administrating active ingredients to elderly subjects, or to any other population that has difficulty in swallowing hard tablets.

The present invention further provides a method for preparing an oral pharmaceutical composition, the method comprising:

i) preparing a mixture comprising (a) an active ingredient being a prescription drug or a drug sold over the counter, and (b) a pharmaceutically acceptable material trapping pressurized gas within cavities thereof; and ii) processing the mixture to obtain an oral pharmaceutical composition that permits the gas to escape upon dissolution, contact with saliva or shattering of the popping material.

The mixture mentioned in (i) above may comprise more than one active ingredient.

According to one embodiment, the mixture prepared in (i) also comprises a pharmaceutically acceptable ingredient (c), preferably an ingredient that melts in the mouth, such as cocoa butter. In such a case, the mixture obtained in (i) preferably includes the ingredients (a) and (b) of the mixture, homogeneously dispersed in ingredient (c), and the processing mentioned in (ii) includes casting of the mixture into molds and cooling to obtain the oral pharmaceutical composition.

According to another embodiment, the mixture prepared in (i) is of powders, and the processing mentioned in (ii) includes compressing the mixture to produce a tablet.

The present invention further provides a method for preparing a gasified oral administration form comprising:

i) melting a pharmaceutically acceptable material to obtain a melt;

ii) adding a gas, at least one active ingredient, and optionally a pharmaceutically acceptable excipient into the melt under superatmospheric pressure to obtain a liquid pharmaceutical composition;

iii) casting the liquid pharmaceutical composition into a mold under superatmospheric pressure;

iv) solidifying the cast pharmaceutical composition under conditions suitable to obtain a gasified oral administration form; and releasing the pressure.

The solidification mentioned above in (iv) may be done in a mold having the form of a desired administration form, for instance, a tablet.

Alternatively, the gasified pharmaceutical composition obtained by the above method in (iii) may be processed to an oral administration form according to the present invention by the following steps:

(iv) solidifying said cast pharmaceutical composition to obtain a solid gasified pharmaceutical composition;

(v) grinding the solid gasified pharmaceutical composition to obtain a popping powder;

(vi) optionally adding excipients to said powder and mixing them together; and (vii) processing the obtained powder or mixture to obtain an oral administration form which produces popping sensation when it is wetted.

The active ingredient used in any of the above methods may be coated or microencapsulated with a taste-masking material, enteric polymers, humidity protective materials, oxidation protective materials etc.

According to another aspect thereof, the present invention provides a method for preparing an oral pharmaceutical composition including a fatty matrix, the method comprising:

(a) melting the fatty matrix;
(b) mixing into the melt matrix the other ingredients of the composition, comprising popping material and at least one OTC or prescription drug;
(c) molding the obtained mixture into a mold; and
(d) cooling the molded mixture as to solidify it.

Preferably, the fatty matrix used in this method melts in the mouth.

The mold according to the invention may be a blister, a hard capsule, a bar-mold, a tablet-mold, or any other kind of mold known in the art.

DETAILED DESCRIPTION OF THE INVENTION

In order to understand the invention and to see how it may be carried out in practice, several specific embodiments will now be described, by way of non-limiting examples only.

Example 1

Preparation of Paracetamol Tablets 500 mg

The following ingredients are used in the preparation of the above-mentioned tablets:
Ingredient mg/tab
Coated Paracetamol 540.0 mg
Popping Candy 300.0 mg
Cross Povidone 30.0 mg
Magnesium Stearate 15.0 mg
Aspartame 10.0 mg
Flavor 10.0 mg Process for the preparation: all the above-mentioned ingredients are mixed together to obtain a uniform mixture that is compressed conventionally to obtain a tablet.

Example 2

Preparation of Calcium Carbonate Lozenges 300 mg

The following ingredients are used in the preparation of the above-mentioned lozenges:
Ingredient mg/loz.
Calcium Carbonate 300.0 mg
Sucrose 100.0 mg
Lactose 100.0 mg
Corn Syrup 50.0 mg
FD&C Red # 40 0.02 mg
Carbon Dioxide q.s.
Grape Flavor 20.0 mg Process for the preparation: sucrose, lactose, coloring agent and corn syrup are melted. Calcium carbonate and flavor are added and mixed together with the molten mixture. Carbon dioxide is bubbled into the molten mixture under superatmospheric pressure. Then, still under superatmospheric pressure, the melt mass is cast to lozenges-shaped molds and cooled.

Example 3

Preparation of Pseudoephedrine Hydrochloride Powder for Reconstitution

The following ingredients are used in the preparation of the above-mentioned powder:
Ingredient mg/g
Coated beads of pseudoephedrine hydrochloride 200.0 mg
Fructose 275.0 mg
Lactose 275.0 mg
Liquid Glucose 225.0 mg
Nitrogen q.s.
Cherry flavor 20.0 mg
FD&C Blue # 1 0.002 mg
FD&C Red # 40 0.001 mg
Saccharin sodium 5.0 mg Process for the preparation: fructose, lactose and liquid glucose are melted. Flavor, sweetener and coloring agents are added and mixed together with the molten mixture. Nitrogen is bubbled into the obtained molten mixture under superatmospheric pressure. Then, the molten mixture is cooled under superatmospheric pressure and then the pressure was released. The obtained solid mixture is ground to obtain a popping powder.

Psuedoephedrine beads are mixed together with the obtained popping powder to yield pseudoephedrine hydrochloride powder.

Example 4

Preparation of Ivermectin 3 mg Capsules

The following ingredients were used in the preparation of the above-mentioned capsules:
Ingredient mg/caps
Ivermectin 3.0 mg
Popping candy 100.0 mg
Magnesium stearate 1.5 mg
Microcrystalline cellulose 150.0 mg Process for the preparation: all the above-mentioned ingredients are mixed together to yield a uniform mixture. The obtained mixture is filled inside hard gelatin capsules.

Example 5

Preparation of Sodium Subsalicylate Melt Bar

The following ingredients are used in the preparation of the above-mentioned bar:
Ingredient mg/Bar
Sodium Subsalicylate 200.0 mg
Popping Candy 1000.0 mg
Cocoa Butter 800.0 mg
Chocolate Flavor 20.0 mg Process for the preparation: Cocoa butter is melted and while cooling, Sodium Subsalicylate, chocolate-flavor and the popping powder are added. The semi-solid mass is cast inside chocolate bar molds to yield the desired bars.

Example 6

Preparation of Lidocaine Oral Gel

The following ingredients were used in the preparation of the above-mentioned gel:
Ingredient % w/w
Lidocaine base 0.2%
Popping Candy (coated with cocoa butter) 20.0%
Propylene Glycol 30.0%
Carbomer 1.0%
Sodium Hydroxide q.s.
Water to 100.0%
Process for the preparation: Carbomer and water are heated and mixed. Sodium Hydroxide is added to form a liquid gel. While cooling, the rest of the materials are added.

Example 7

Preparation of Ibuprofen 250 mg Tablet

Ingredient mg/tab
Coated Ibuprofen 270 mg
Hard Fat 500 mg
Strawberry Flavor 3 mg
Aspartame 5 mg
Popping Candy 200 mg
Process for the preparation: Ibuprofen, Strawberry flavor and Aspartame are mixed in Hard Fat heated to 45° C. The mixture is cooled to 38° C. and Popping Candy is added. Mixture is filled inside blisters.

Popping candy is very sensitive to humidity and moisture. Immediately when exposed to moisture it elevates the entrapped gas. Popping candy is also quite sensitive to pressure, which might break the walls of the cavities that entrap the pressurized gas. The above mentioned formulation does not require pressing the popping candy during preparation, and protects it from humidity penetration during storage. When the bar is chewed or even only wets in the mouth, the popping candy gives a "jumping" sensation. This phenomenon is popular among children and may improve compliance to take the drug.

Example 8

Aspirin 100 mg Chewable Tablet

Ingredient mg/tab
Aspirin 100 mg
Hydrogenated Palm Oil 500 mg
Strawberry Flavor 3 mg
Aspartame 5 mg
Starch 4 mg
Process for the preparation: Aspirin, Strawberry flavor, Starch and Aspartame are mixed in Hydrogenated Palm Oil heated to 60° C. The mixture is cooled to 45° C. and filled inside blisters.

Example 9

Preparation of Amoxycillin 250 mg Chewable Tablet

Ingredient mg/tab
Amoxycillin 250 mg
Hard Fat 600 mg
Vanilla Flavor 3 mg
Aspartame 5 mg
Popping Candy 250 mg
Process for the preparation: Amoxycillin, Vanilla flavor and Aspartame are mixed in Hard Fat heated to 45° C. The mixture is cooled to 38° C. and Popping Candy is added. Mixture is filled inside blisters.

Example 10

Preparation of Dexrtomethorphan Oral Suspension

The following ingredients are used in the preparation of the above-mentioned suspension:
Ingredient mg/5 ml
Coated Dextromethorphan Hydrobromide 30.0 mg
Popping Candy 100.0 mg
Cherry Flavor 0.2 mg
Peanut Oil to 5.0 ml Process for the preparation: all the above-mentioned ingredients are mixed together to obtain a uniform mixture that is filled inside a bottle.

The invention claimed is:
1. An oral pharmaceutical composition consisting of:
one or more active ingredients;
a popping material; and
an optional flavoring agent;
said popping material consisting of a pharmaceutically acceptable material consisting of one or more cavities with thermodynamically stable pressurized gas being trapped in cavities thereof in a manner that allows its escape upon dissolution, contact with saliva or shattering of the popping material,
wherein
said gas being selected from carbon dioxide, nitrogen, air, helium, argon, and neon, said active ingredient is a prescription drug or a drug sold over the counter and wherein said active ingredient is selected from the group consisting of expectorant, analgesic, antipyretic, anti-inflammatory, anti-hypertensive, anti-anginal, antiepileptic, anxiolytic, antipsychotic, anti-allergic, antidepressant, anti-histamine, hormone, steroid, hypolipidaemic and diuretic agents and said active ingredient is coated by a coating.

2. An oral pharmaceutical composition according to claim 1, wherein said one or more active ingredients is included in the pharmaceutically acceptable material in which gas is entrapped.

3. An oral pharmaceutical composition according to claim 1, wherein said pharmaceutically acceptable material is selected from sugars, corn syrup or mixtures thereof.

4. An oral pharmaceutical composition according to claim 1, wherein said one or more active ingredients are selected from paracetamol, diphenhydramine, dextromethorphan, loratadine, lidocaine, ibuprofen, pseudoephedrine, enalapril, calcium carbonate, isosorbide-mononitrate, enalapril maleate, sodium valporate, aspirin, alprazolam, amitriptyline, benzocaine, celecoxib, dexamethazone, famotidine, simvastatin, lorazepam, testosterone, and verapamil.

5. An oral pharmaceutical composition according to claim 1, suitable for veterinary use.

6. An oral pharmaceutical composition according to claim 5, wherein said one or more active ingredients are selected from nitroscanate, abamectin and ivermectin.

7. An oral pharmaceutical composition according to claim 1, having a form of a tablet, powder, pellet, capsule, syrup, oil, suspension, gel, drops, or losenge.

8. An oral pharmaceutical composition according to claim 1, having a form of a semi-solid, or oil suspension to enhance disintegration or dissolution of the active ingredient.

9. An oral pharmaceutical composition according to claim 1, wherein said coating is a a taste-masking material, a biodegradable polymer, an enteric polymer, a humidity protective material, an oxidation protective material-or a mixture thereof.

10. An oral pharmaceutical composition according to claim 1, wherein said coating is a taste masking coating.

11. A method for preparing an oral pharmaceutical composition according to claim 1 comprising:
  (i) preparing a mixture consisting of (a) one or more active ingrediences being prescription drugs or drugs sold over the counter, and (b) a pharmaceutically acceptable material trapping pressurized gas within cavities thereof; and
  (ii) processing said mixture to obtain an oral pharmaceutical composition that permits said gas to escape upon dissolution, contact with saliva or shattering of the popping material.

* * * * *